United States Patent
Knauf-Beiter et al.

[11] Patent Number: 6,011,064
[45] Date of Patent: Jan. 4, 2000

[54] MICROBICIDAL COMPOSITIONS

[75] Inventors: Gertrude Knauf-Beiter, Müllheim; Ronald Zeun, Neuenburg, both of Germany

[73] Assignee: Novartis Crop Protection, Inc., Greensboro, N.C.

[21] Appl. No.: 08/981,436

[22] PCT Filed: Jun. 4, 1996

[86] PCT No.: PCT/EP96/02420

§ 371 Date: Dec. 16, 1997

§ 102(e) Date: Dec. 16, 1997

[87] PCT Pub. No.: WO97/00011

PCT Pub. Date: Jan. 3, 1997

[30] Foreign Application Priority Data

Jun. 16, 1995 [CH] Switzerland ............... 1786/95
Jun. 21, 1995 [CH] Switzerland ............... 1822/95

[51] Int. Cl.[7] .......... A01N 37/12; A01N 37/44; A01N 43/08; A01N 43/76

[52] U.S. Cl. .......... 514/538; 514/376; 514/471; 514/539

[58] Field of Search ............... 514/538, 539, 514/376, 471

[56] References Cited

U.S. PATENT DOCUMENTS

| | | | |
|---|---|---|---|
| 4,829,085 | 5/1989 | Wenderoth et al. | 514/522 |
| 5,194,662 | 3/1993 | Brand et al. | 560/35 |
| 5,723,491 | 3/1998 | Nuninger et al. | 514/538 |

FOREIGN PATENT DOCUMENTS

| | | |
|---|---|---|
| 253213 | 1/1988 | European Pat. Off. . |
| 370629 | 5/1990 | European Pat. Off. . |
| 414153 | 2/1991 | European Pat. Off. . |
| 460575 | 12/1991 | European Pat. Off. . |
| 463488 | 1/1992 | European Pat. Off. . |
| 90/07493 | 7/1990 | WIPO . |

OTHER PUBLICATIONS

Derwent Abstract 91–363072/199150 of EP 460575 (1991).
Worthing et al, The Pesticide Manual, 9th Ed. (1991) pp. 554–555.

*Primary Examiner*—Allen J. Robinson
*Attorney, Agent, or Firm*—Michael P. Morris; John D. Peabody, III

[57] ABSTRACT

A phytomicrobicidal composition comprising such an amount of at least two active ingredient components that a synergistic effect is achieved, together with a suitable carrier material, wherein component I is a compound of the formula I

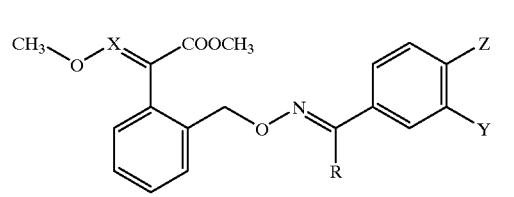

in which:

X is CH or N;

R is $CH_3$ or cyclopropyl;

Y is H, F, Cl, Br, $CF_3$, $CF_3O$, propargyloxy;

Z is H, F, Cl, $CF_3$, $CF_3O$; or

Y and Z together are a methylenedioxy, a (difluoromethylene)dioxy, an ethylenedioxy, a (trifluoroethylene)dioxy or a benzo group;

and wherein component II is a compound selected from the group consisting of II A) metalaxyl, IIB) R-metalaxyl, II C) furalaxyl, II D) benalaxyl, II E) ofurace, II F) oxadixyl, II G) cymoxanil and II H) mancozeb.

10 Claims, No Drawings

MICROBICIDAL COMPOSITIONS

This application is a 371 of PCT/EP 96/02420, filed Jun. 4, 1996.

The present invention relates to novel crop-protecting mixtures of active ingredients having a synergistically increased microbicidal action and comprising at least two active components, and to methods of using such mixtures in crop protection, in particular for controlling and preventing the incidence of diseases.

Component I is a compound of the formula I

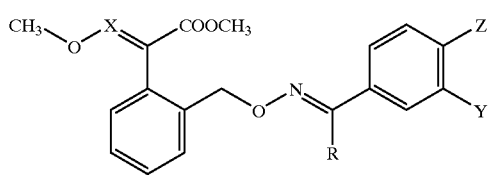

in which:
X is CH or N;
R is $CH_3$ or cyclopropyl;
Y is H, F, Cl, Br, $CF_3$, $CF_3O$, propargyloxy;
Z is H, F, Cl, $CF_3$, $CF_3O$; or
Y and Z together are a methylenedioxy, a (difluoromethylene)dioxy, an ethylenedioxy, a (trifluoroethylene)dioxy or a benzo group.

These compounds have been described in EP-A-403 618, EP-A-460 575, WO 92/18494 and other publications.

Component II is a compound selected from the group consisting of

II A) methyl N-(2-methoxyacetyl)-N-(2,6-xylyl)-DL-alaninate ("metalaxyl"; GB-1 500 581), in particular its R enantiomer, II B) methyl N-(2-methoxyacetyl)-N-(2,6-xylyl)-D-alaninate ("R-metalaxyl"; GB-1 500 581), II C) methyl N-(2-furoyl)-N-(2,6-xylyl)-DL-alaninate ("furalaxyl"; GB-1 448 810), II D) methyl N-phenylacetyl-N-2,6-xylyl-DL-alaninate ("benalaxyl"; DE-29 03 612), II E) (±)-α-(2-chloro-N-2,6-xylylacetamido)-γ-butyrolactone ("ofurace"; U.S. Pat. No. 4,141,989), II F) 2-methoxy-N-(2-oxo-1,3-oxazolidin-3-yl)-acet-2',6'-xylidide ("oxadixyl"; GB-P. 2 058 059), II G) 1-(2-cyano-2-methoxyiminoacetyl)-3-ethylurea, ("cymoxanil"; U.S. Pat. No. 3,957,847) and II H) manganese ethylenebis(dithiocarbamate) polymer zinc complex ("mancozeb"; U.S. Pat. No. 2,974,156).

The invention furthermore relates to mixtures in which in component I of the formula I:
X is CH or N;
R is $CH_3$ or cyclopropyl;
Y is H, F, Cl, Br, $CF_3$, $CF_3O$, propargyloxy;
Z is H, F, Cl; or
Y and Z together are a methylenedioxy, a (difluoromethylene)dioxy, an ethylenedioxy, a (trifluoroethylene)dioxy or a benzo group; and in which component II is a compound selected from the group consisting of II A) methyl N-(2-methoxyacetyl)-N-(2,6-xylyl)-DL-alaninate ("metalaxyl"), in particular its R enantiomer, II B) methyl N-(2-methoxyacetyl)-N-(2,6-xylyl)-D-alaninate ("R-metalaxyl"), II C) methyl N-(2-furoyl)-N-(2,6-xylyl)-DL-alaninate ("furalaxyl"), II D) methyl N-phenylacetyl-N-2,6-xylyl-DL-alaninate ("benalaxyl"), II E) (±)-α-(2-chloro-N-2,6-xylylacetamido)-γ-butyrolactone ("ofurace"), II F) 2-methoxy-N-(2-oxo-1,3-oxazolidin-3-yl)-acet-2',6'-xylidide ("oxadixyl"), and II G) 1-(2-cyano-2-methoxyiminoacetyl)-3-ethylurea ("cymoxanil").

Surprisingly, it has emerged that in the prevention and control of plant diseases the mixtures according to the invention, of components I and II, not only exert a mutually complementary action against a variety of target pathogens or a purely additive action against the same pathogens, but that they display a pronounced, synergistically increased action.

Advantageous mixing ratios of the two active ingredients are I:II=25:1 to 1:20, preferably I:II=20:1 to 1:10 and 12:1 to 1:8.

Particularly advantageous mixing ratios are
I:IIA=10:1 to 1:10
I:IIB=10:1 to 1:8
I:IIC=6:1 to 1:8
I:IID=8:1 to 1:4
I:IIE=10:1 to 1:6
I:IIF=10:1 to 1:8
I:IIG=10:1 to 1:5
I:IIH=1:30 to 1:1

Preferred two-component mixtures are those in which component I is selected from the group consisting of the following compounds:

(01) methyl 3-methoxy-2-[α-{[(α-cyclopropyl-3-trifluoromethylbenzyl)imino]oxy}-o-tolyl]acrylate;

(02) methyl 3-methoxy-2-[α-{[(α-cyclopropyl-3,4-(difluoromethylenedioxy)benzyl)-imino]oxy}-o-tolyl] acrylate;

(03) methyl 2-[α-{[(α-methyl-3-bromobenzyl)imino] oxy}-o-tolyl]glyoxylate O-methyloxime;

(04) methyl 2-[α-{[(α-cyclopropyl-3,4-methylenedioxybenzyl)imino]oxy}-o-tolyl]glyoxylate O-methyloxime;

(05) methyl 3-methoxy-2-[α-{[(α-methyl-3-propargyloxybenzyl)imino]oxy}-o-tolyl]acrylate;

(06) methyl 2-[α-{[(α-methyl-3,4-(difluoromethylenedioxy)benzyl)imino]-oxy}-o-tolyl] glyoxylate O-methyloxime;

(07) methyl 3-methoxy-2-[α-{[(α-cyclopropyl-3,4-methylenedioxybenzyl)imino]oxy}-o-tolyl]acrylate;

(08) methyl 2-[α-{[(α-methyl-3-propargyloxybenzyl) imino]oxy}-o-tolyl]glyoxylate O-methyloxime;

(09) methyl 2-[α-{[(α-cyclopropyl-4-fluorobenzyl) imino]oxy}-o-tolyl]glyoxylate O-methyloxime;

(10) methyl 2-[α-{[(α-methyl-4-fluoro-3-trifluoromethylbenzyl)imino]oxy}-o-tolyl]glyoxylate O-methyloxime;

(11) methyl 3-methoxy-2-[α-{[(1-(β-naphthyl)ethyl) imino]oxy}-o-tolyl]acrylate;

(12) methyl 3-methoxy-2-[α-{[(α-methyl-3,4-methylenedioxybenzyl)imino]oxy}-o-tolyl]acrylate;

(13) methyl 2-[α-{[(α-methyl-3-chlorobenzyl)imino]oxy}-o-tolyl]glyoxylate O-methyloxime;

(14) methyl 3-methoxy-2-[α-{[(α-methyl-3,4-ethylenedioxybenzyl)imino]oxy}-o-tolyl]acrylate;

(15) methyl 2-[α-{[(α-cyclopropyl-4-chlorobenzyl)imino]oxy}-o-tolyl]glyoxylate O-methyloxime;

(16) methyl 3-methoxy-2-[α-{[(α-cyclopropyl-3-chlorobenzyl)imino]oxy}-o-tolyl]acrylate;

(17) methyl 2-[α-{[(α-cyclopropyl-3-trifdluoromethylbenzyl)imino]oxy}-o-tolyl]glyoxylate O-methyloxime;

(18) methyl 3-methoxy-2-[α-{[(α-methyl-3-trifluoromethoxybenzyl)imino]oxy}-o-tolyl]acrylate;

(19) methyl 2-[α-{[(α-methyl-3,4-methylenedioxybenzyl)imino]oxy}-o-tolyl]glyoxylate O-methyloxime;

(20) methyl 2-[α-{[(α-cyclopropyl-3,4-(difluoromethylenedioxy)benzyl)imino]oxy}-o-tolyl]glyoxylate O-methyloxime;

(21) methyl 2-[α-{[(α-methyl-3,4-ethylenedioxybenzyl)imino]oxy}-o-tolyl]glyoxylate O-methyloxime;

(22) methyl 3-methoxy-2-[α-{[(1-(2,3-dihydro-2,2,3-trifluoro-1,4-benzodioxan-6-yl)ethyl)imino]oxy}-o-tolyl]acrylate;

(23) 2-[α-{[(1-(2,3-dihydro-2,2,3-trifluoro-1,4-benzodioxan-6-yl)ethyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(25) methyl 2-[α-{[(α-methyl-4-chlorobenzyl)imino]oxy}-o-tolyl]glyoxylate O-methyloxime;

(26) methyl 3-methoxy-2-[α-{[(α-methyl-4-chlorobenzyl)imino]oxy}-o-tolyl]acrylate;

(27) methyl 3-methoxy-2-[α-{[(α-methyl-3-bromobenzyl)imino]oxy}-o-tolyl]acrylate;

(28) methyl 2-[α-{[(1-(α-naphthyl)ethyl)imino]oxy}-do-tolyl]glyoxylate O-methyloxime;

(29) methyl 3-methoxy-2-[α-{[(α-methyl-3,4-(difluoromethylenedioxy)benzyl)imino]oxy}-o-tolyl]acrylate;

(30) methyl 3-methoxy-2-[α-{[(α-cyclopropyl-4-fluorobenzyl)imino]oxy}-o-tolyl]acrylate;

(31) methyl 3-methoxy-2-[α-{[(α-methyl-4-fluoro-3-tnfluoromethylbenzyl)imino]oxy}-o-tolyl]acrylate;

(32) methyl 2-[α-{[(α-methyl-3-trifluoromethoxybenzyl)imino]oxy}-o-tolyl]glyoxylate O-methyloxime;

(33) methyl 2-[α-{[(α-cyclopropyl-3-chlorobenzyl)imino]oxy}-o-tolyl]glyoxylate O-methyloxime;

(34) methyl 3-methoxy-2-[α-{[(α-methyl-3-chlorobenzyl)imino]oxy}-o-tolyl]acrylate;

(35) methyl 2-[α-{[(α-methyl-3-trifluoromethylbenzyl)imino]oxy}-o-tolyl]glyoxylate O-methyloxime;

(36) methyl 3-methoxy-2-[α-{[(α-cyclopropyl-4-chlorobenzyl)imino]oxy}-o-tolyl]acrylate;

(37) methyl 2-[α-{[(α-cyclopropyl-4-trifluoromethylbenzyl)imino]oxy}-o-tolyl]glyoxylate O-methyloxime;

(38) methyl 2-[α-{[(α-cyclopropyl-4-trifluoromethoxybenzyl)imino]oxy}-o-tolyl]glyoxylate O-methyloxime.

The following are particularly preferred amongst these:

(25) methyl 2-[α-{[(α-methyl-4-chlorobenzyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(32) methyl 2-[α-{[(α-methyl-3-trifluoromethoxybenzyl)imino]oxy}-o-tolyl]glyoxylate O-methyloxime;

(12) methyl 3-methoxy-2-[α-{[(α-methyl-3,4-methylenedioxybenzyl)imino]oxy}-o-tolyl]acrylate;

(09) methyl 2-[α-{[(α-cyclopropyl-4-fluorobenzyl)imino]oxy}-o-tolyl]glyoxylate O-methyloxime;

(26) methyl 3-methoxy-2-[α-{[(α-methyl-4-chlorobenzyl)imino]oxy}-o-tolyl]acrylate;

(18) methyl 3-methoxy-2-[α-{[(α-methyl-3-trifluoromethoxybenzyl)imino]oxy}-o-tolyl]acrylate;

(35) methyl 2-[α-{[(α-methyl-3-trifluoromethylbenzyl)imino]oxy}-o-tolyl]glyoxylate O-methyloxime;

(15) methyl 2-[α-{[(α-cyclopropyl-4-chlorobenzyl)imino]oxy}-o-tolyl]glyoxylate O-methyloxime;

(36) methyl 3-methoxy-2-[α-{[(α-cyclopropyl-4-chlorobenzyl)imino]oxy}-o-tolyl]acrylate;

(37) methyl 2-[α-{[(α-cyclopropyl-4-trifluoromethylbenzyl)imino]oxy}-o-tolyl]glyoxylate O-methyloxime;

(38) methyl 2-[α-{[(α-cyclopropyl-4-trifluoromethoxybenzyl)imino]oxy}-o-tolyl]glyoxylate O-methyloxime.

Particularly advantageous mixtures result when a component of the formula I is employed with either metalaxyl as component II, but in particular with the enantiomeric R-metalaxyl II B in at least 85% pure form (remainder S-enantiomer).

Other preferred mixtures are those in which component II is cymoxanil or mancozeb.

Also advantageous are mixtures of components I and II which comprise mancozeb as an additional, third component.

The active ingredient mixtures I+II according to the invention have highly advantageous properties protecting plants against the incidence of disease. Using the present active ingredient mixtures, the microorganisms which are found on plants or parts of plants (fruits, flowers, foliage, stalks, tubers, roots) of a variety of crops of useful plants can be contained or destroyed, and even parts of plants which grow at a later point in time remain unharmed by such microorganisms. They can also be used as seeddressing materials for the treatment of plant propagation material, in particular seed (fruits, tubers, kernels) and nursery plants (for example rice) for protecting them against fungal infections and against soil-borne phytopathogenic fungi. The active ingredient mixtures according to the invention are distinguished by the fact that they are well tolerated by plants and by being environmentally friendly.

As a result of the presence of typical preparations for controlling Oomycetes (for example Phytophthora, Peronospora, Bremia, Pythium, Plasmopara) as component II, the mixtures according to the invention are distinguished by a high efficacy against these pests. However, the active ingredient mixtures are furthermore active against the phytopathogenic fungi which belong to the following classes: Ascomycetes (for example Venturia, Podosphaera, Erysiphe, Monilinia, Mycosphaerella, Uncinula); Basidiomycetes (for example the species Hemileia, Rhizoctonia, Puccinia); and Fungi imperfecti (for example Botrytis, Helminthosporium, Rhynchosporium, Fusarium, Septoria, Cercospora, Alternaria, Pyricularia and, in particular, Pseudocercosporella herpotrichoides).

Examples of plant species which are suitable as target crops for the indications disclosed here are, within the scope of the present invention, the following: cereals (wheat, barley, rye, oats, rice, sorghum and related species); beet (sugar and fodder beet); pomaceous fruit, stone fruit, soft fruit (apples, pears, plums, peaches, almonds, cherries, strawberries, raspberries and blackberries); leguminous plants (beans, lentils, peas, soya); oil crops (oilseed rape, mustard, poppies, olives, sunflowers, coconut, castor, cocoa, groundnuts); cucurbits (pumpkins, cucumbers, melons); fibre plants (cotton, flax, hemp, jute); citrus fruit (oranges, lemons, grapefruit, tangerines); vegetables (spinach, lettuce, asparagus, cabbages, carrots, onions, tomatoes, potatoes, bell peppers); Lauraceae (avocado, Cinnamonum, camphor) or plants such as maize, tobacco, nuts, coffee, sugar cane, tea, grapevines, hops, Musaceae and latex plants, and also ornamentals (flowers, shrubs, deciduous trees and coniferous trees such as conifers). This enumeration is not limiting.

The active ingredient mixtures according to the invention are particularly advantageous for use in crops which are endangered by Oomycetes, i.e. those which are damaged by various species of downy mildew. These crops include grapevines, potatoes, tobacco, vegetables (for example tomatoes, courgettes, cucumbers, avocados) and fruit such as citrus fruit; hops, sugar beet, bananas, maize, ornamental lawn (turf) and others. Propagation material (such as seed) of leguminous plants (peas, beans, lentils), of maize, sorghum and sunflowers can furthermore be protected with the active ingredient mixtures, in particular against attack by Peronosporaceae. In addition, however, these mixtures can also be employed advantageously in other crops, especially in cereals such as wheat and barley, as already mentioned above.

The mixtures of the active ingredients of the formulae I and II are usually used in the form of combinations. The active ingredients of the formulae I and II can be applied to the area or plant to be treated either simultaneously, or one after the other on the same day, if desired together with other carriers, surfactants or other application-enhancing additives conventionally used in the art of formulation. Suitable carriers and additives can be solid or liquid and are those substances which are expedient in the art of formulation, for example natural or regenerated mineral substances, solvents, dispersants, wetting agents, adhesives, thickeners, binders and fertilizers.

A preferred method of applying an active ingredient mixture which comprises in each case at least one of these active ingredients I and II is application to the aerial parts of the plants, especially the foliage (foliar application). Number and rates of application depend on the biological and climatic environment of the pathogen. Alternatively, the active ingredient can reach the plant via the soil or the water through the root system (systemic action), by drenching the locus of the plant with a liquid preparation (for example in rice growing) or by incorporating the substances into the soil in solid form, for example in the form of granules (soil application). The compounds of the formulae I and II can also be applied to seed kernels for the purposes of seed treatment (coating), either by soaking the tubers or kernels in succession with a liquid preparation of an active ingredient or by coating them with a pre-combined moist or dry preparation. In addition, other types of application to plants are possible in specific cases, for example the specific treatment of buds or the fruiting heads. The compounds of the combination are employed as pure active ingredients or, preferably, together with the auxiliaries conventionally used in the art of formulation, and they are therefore processed in a known manner to give, for example, emulsion concentrates, spreadable pastes, directly sprayable or dilutable solutions, dilute emulsions, wettable powders, soluble powders, dusts, granules, or by means of encapsulations, for example in polymers. The application methods, such as spraying, atomizing, dusting, scattering, brushing or pouring, and the nature of the compositions, are selected to suit the intended aims and the prevailing circumstances. Advantageous rates of application of the active ingredient mixture are generally 20 g to 1000 g of a.i./ha, in particular 50 g to 800 g of ai./ha, particularly preferably 100 g to 700 g of ai./ha. The rates of application for seed treatment are 0.5 g–800 g, preferably 5 g–100 g, of a.i. per 100 kg of seed.

The formulations are prepared in a known manner, for example by intimately mixing and/or grinding the active ingredients with extenders, for example with solvents, solid carriers, and, if appropriate, surface-active compounds (surfactants).

The following are possible solvents: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or parafins, alcohols and glycols and their ethers and esters such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or dimethylformamide, and epoxidized or unepoxidized vegetable oils, such as epoxidized coconut oil or soya oil; or water.

Solid carriers which are generally used, for example for dusts and dispersible powders, are ground natural minerals, such as calcite, talc, kaolin, montmorillonite or attapulgite. To improve the physical properties, it is also possible to add highly disperse silica or highly disperse absorptive polymers. Possible particulate, adsorptive carriers for granules are the porous types, for example pumice, brick, grit, sepiolite or bentonite, or non-sorptive carrier materials, for example calcite or sand. In addition, a large number of pregranulated materials of inorganic or organic nature can be used such as, in particular, dolomite or comminuted plant residues.

Depending on the nature of the active ingredients of the formulae I and II to be formulated, surface-active compounds which are suitable are non-ionic, cationic and/or anionic surfactants which have good emulsifying, dispersing and wetting properties. Surfactants are also to be understood as meaning mixtures of surfactants.

Particularly advantageous adjuvants which enhance application are furthermore natural or synthetic phospholipids from the series of the cephalins and lecithins, for example phosphatidylethanolamine, phosphatidylserine, phosphatidylglycerine, lysolecithin.

As a rule, the agrochemical preparations comprise 0.1 to 99%, in particular 0.1 to 95%, of active ingredients of the formulae I and II, 99.9 to 1%, in particular 99.9 to 5%, of a solid or liquid additive and 0 to 25%, in particular 0.1 to 25%, of a surfactant.

While concentrated compositions are more preferred as commercial products, the end user tends to use dilute compositions.

Such compositions are part of the present invention.

The examples which follow are intended to illustrate the invention, "active ingredient" being understood as meaning a mixture of compound I and compound II (in particular metalaxyl II A, preferably R-metalaxyl II B) in a specific mixing ratio.

FORMULATION EXAMPLES

| Wettable powders | a) | b) | c) |
|---|---|---|---|
| Active ingredient [I:II = 4:1(a), 1:4(b), 3:2(c)] | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active ingredient is mixed thoroughly with the additives and the mixture is ground in a suitable mill. This gives wettable powders which can be diluted with water to give suspensions of any desired concentration.

| Emulsion concentrate | |
|---|---|
| Active ingredient (I:II = 3:7) | 10% |
| Octylphenolpolyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired dilution which can be employed in crop protection can be prepared from this concentrate by diluting it with water.

| Dusts | a) | b) | c) |
|---|---|---|---|
| Active ingredient [I:II = 2:3(a); 5:1(b) and 1:1(c)] | 5% | 6% | 4% |
| Talc | 95% | — | — |
| Kaolin | — | 94% | — |
| Rock meal | — | — | 96% |

Ready-to-use dusts are obtained by mixing the active ingredient with the carrier and grinding the mixture in a suitable mill. Such powders can also be used for dry seed-dressing.

| Extruder granules | |
|---|---|
| Active ingredient (I:II = 4:11) | 15% |
| Sodium lignosulfonate | 2% |
| Carboxymethylcellulose | 1% |
| Kaolin | 82% |

The active ingredient is mixed with the additives, and the mixture is ground and moistened with water. This mixture is extruded and subsequently dried in a stream of air.

| Coated granules | |
|---|---|
| Active ingredient (I:II = 7:1) | 8% |
| Polyethylene glycol (MW 200) | 3% |
| Kaolin | 89% |
| (MW = molecular weight) | |

In a mixer, the finely ground active ingredient is applied uniformly to the kaolin which has been moistened with polyethylene glycol. In this manner, dust-free coated granules are obtained.

| Suspension concentrate | |
|---|---|
| Active ingredient (I:II = 3:1) | 40% |
| Propylene glycol | 10% |
| Nonylphenol polyethylene glycol ether (15 mol of ethylene oxide) | 6% |
| Sodium lignosulfonate | 10% |
| Carboxymethylcellulose | 1% |
| Silicone oil (in the form of a 75% aqueous emulsion) | 1% |
| Water | 32% |

The fmely-ground active ingredient is mixed intimately with the additives. This gives a suspension concentrate from which suspensions of any desired dilution can be prepared by diluting it with water. Such dilutions can be used for treating live plants and plant propagation material by spraying, pouring or immersing, thus protecting them against microbial attack.

BIOLOGICAL EXAMPLES

A synergistic effect is present when the activity of the active ingredient combination exceeds the total of the activities of the individual components.

The activity E to be expected for a given active ingredient combination obeys the so-called COLBY formula and can be calculated as follows (COLBY, S. R. "Calculating synergistic and antagonistic responses of herbicide combinations", Weeds, Vol. 15, pages 20–22; 1967):

if ppm=milligrams of active ingredient (=a.i.) per liter of spray mixture

X=% activity caused by active ingredient I when p ppm of active ingredient are applied Y=% activity caused by active ingredient II when q ppm of active ingredient is applied E=expected activity of the active ingredients I+II when p+q ppm of active ingredient is applied (additive effect), then Colby's formula reads:

$$E = X + Y - \frac{X \cdot Y}{100}$$

If the actually observed activity (O) exceeds the expected activity (E), then the activity of the combination is superadditive, i.e. a synergistic effect is present. O/E= synergism factor (SF).

In the examples which follow, the disease level of the untreated plants is equated to 100%, which corresponds to an activity of 0%.

B-1: Activity Against *Puccinia Recondita* in Wheat a) Residual-protective Action 6 days after sowing, wheat plants are sprayed to drip point with an aqueous spray mixture prepared with a wettable powder of the active ingredient mixture (0.02% of active ingredient) and, 24 hours later, infected with a uredo spore suspension of the fungus. After an incubation time of 48 hours (conditions: 95 to 100 percent relative atmospheric humidity at 20°), the plants are placed in a greenhouse at 22°. 12 days after the infection, the fungus infestation is assessed.

b) Systemic Action

An aqueous spray mixture is prepared with a wettable powder of the active ingredient mixture (0.006% of active ingredient based on the soil volume) is poured next to wheat plants 5 days after sowing. Care is taken that the spray mixture does not come into contact with aerial parts of the plants. 48 hours later, the plants are infected with a uredo spore suspension of the fungus. After an incubation time of 48 hours (conditions: 95 to 100 percent relative atmospheric humidity at 20°), the plants are placed in a greenhouse at 22°. 12 days after the infection, the fungus infestation is assessed.

A good synergistic effect is shown in particular by active ingredient mixtures in which component I is

(29) methyl 3-methoxy-2-[α-{[(α-methyl-3,4-(difluoromethylenedioxy)benzyl)imino]oxy}-o-tolyl]acrylate;

(18) methyl 3-methoxy-2-[α-{[(α-methyl-3-trifluoromethoxybenzyl)imino]oxy}-o-tolyl]acrylate;

(09) methyl 2-[α-{[(α-cyclopropyl-4-fluorobenzyl)imino]oxy}-o-tolyl]glyoxylate O-methyloxime;

(32) methyl 2-[α-{[(α-methyl-3-trifluoromethoxybenzyl)imino]oxy}-o-tolyl]glyoxylate O-methyloxime;

(15) methyl 2-[α-{[(α-cyclopropyl-4-chlorobenzyl)imino]oxy}-o-tolyl]glyoxylate O-methyloxime;

(35) methyl 2-[α-{[(α-methyl-3-trifluoromethylbenzyl)imino]oxy}-o-tolyl]glyoxylate O-methyloxime; or (6) methyl 2-[α-{[(α-methyl-3,4-(difluoromethylenedioxy)benzyl)imino]oxy}-o-tolyl]glyoxylate O-methyloxime.

Example B-2: Activity Against Plasmopara Viticola in Grapevines

Grapevine seedlings at the 4-to-5-leaf stage are sprayed to drip point with an aqueous spray mixture prepared with a wettable powder of the active ingredient mixture (0.02% of active ingredient) and, 24 hours later, infected with a sporangia suspension of the fungus. The fungus infestation is assessed 6 days after infection, during which time a relative atmospheric humidity of 95 to 100% and a temperature of 20° are maintained.

A marked synergistic effect is shown, in particular, by active ingredient mixtures in which component I is

(12) methyl 3-methoxy-2-[α-{[(α-methyl-3,4-methylenedioxybenzyl)imino]oxy}-o-tolyl]acrylate;

(18) methyl 3-methoxy-2-[α-{[(α-methyl-3-trifluoromethoxybenzyl)imino]oxy}-o-tolyl]acrylate;

(32) methyl 2-[α-{[(α-methyl-3-trifluoromethoxybenzyl)imino]oxy}-o-tolyl]glyoxylate O-methyloxime;

(15) methyl 2-[α-{[(α-cyclopropyl-4-chlorobenzyl)imino]oxy}-o-tolyl]glyoxylate O-methyloxime;

(6) methyl 2-[α-{[(α-methyl-3,4-(difluoromethylenedioxy)benzyl)imino]oxy}-o-tolyl]glyoxylate O-methyloxime or

(35) methyl 2-[α-{[(α-methyl-3-trifluoromethylbenzyl)imino]oxy}-o-tolyl]glyoxylate O-methyloxime;

and in which component II is ofurace (II E), oxadixyl (II F), or in particular metalaxyl (II A) or R-metalaxyl (II B).

Example B-3: Residual-protective Action Against Venturia Inaegualis in Apples

Apple cuttings with fresh shoots 10 to 20 cm in length are sprayed to drip point with an aqueous spray mixture prepared with a wettable powder of the active ingredient mixture (0.02% of active ingredient) and, 24 hours later, infected with a conidia suspension of the fungus. The plants are incubated for 5 days at a relative atmospheric humidity of 90 to 100% and placed in a greenhouse at 20 to 24° for a further 10 days. The fungus infestation is assessed 12 days after the infection.

The active ingredient mixtures according to the invention have a markedly increased activity.

Example B-4: Activity Against Erysidphe Diradminis in Barley a) Residual-protective Action Barley plants approximately 8 cm high are sprayed to drip point with an aqueous spray mixture prepared with a wettable powder of the active ingredient (0.02% of active ingredient) and, 3 to 4 hours later, dusted with conidia of the fungus. The infected plants are placed in a greenhouse at 22°. The fungus infestation is assessed 12 days after the infection.

b) Systemic Action

An aqueous spray mixture prepared with a wettable powder of the active ingredient (0.002% of active ingredient based on the soil volume) is poured next to barley plants approximately 8 cm high. Care is taken that the spray mixture does not come into contact with the aerial parts of the plants. 48 hours later, the plants are dusted with conidia of the fungus. The infected plants are placed in a greenhouse at 22°. The fungus infestation is assessed 12 days after the infection.

A good synergistic effect is shown, in particular, by active ingredient mixtures in which component (I) is (6) methyl 2-[α-{[(α-methyl-3,4-(difluoromethylenedioxy)benzyl)imino]oxy}-o-tolyl]glyoxylate O-methyloxime;

(09) methyl 2-[α-{[(α-cyclopropyl-4-fluorobenzyl)imino]oxy}-o-tolyl]glyoxylate O-methyloxime;

(32) methyl 2-[α-{[(α-methyl-3-trifluoromethoxybenzyl)imino]oxy}-o-tolyl]glyoxylate O-methyloxime;

(15) methyl 2-[α-{[(α-cyclopropyl-4-chlorobenzyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(25) methyl 2-[α-{[(α-methyl-4-chlorobenzyl)imino]oxy}-o-tolyl]glyoxylate O-methyloxime;

(35) methyl 2-[α-{[(α-methyl-3-trifluoromethylbenzyl)imino]oxy}-o-tolyl]glyoxylate O-methyloxime;

(18) methyl 3-methoxy-2-[α-{[(α-methyl-3-trifluoromethoxybenzyl)imino]oxy}-o-tolyl]acrylate;

(36) methyl 3-methoxy-2-[α-{[(α-cyclopropyl-4-chlorobenzyl)imino]oxy}-o-tolyl]acrylate or

(37) methyl 2-[α-[{(α-cyclopropyl-4-trifluoromethylbenzyl)imino]oxy}-o-tolyl]glyoxylate O-methyloxime.

Example B-5: Activity Against Phytodhthora Infestans in Tomatoes a) Curative Action Tomato plants cv. "Roter Gnom" are grown for three weeks and then sprayed with a zoospore suspension of the fungus and incubated in a cabin at 18 to 20° and saturated atmospheric humidity. The humidification is interrupted after 24 hours. After the plants have dried, they are sprayed with a mixture which comprises the active ingredient formulated as a wettable powder at a concentration of 200 ppm. After the spray coating has dried, the plants are returned to the humid chamber for 4 days. Number and size of the typical foliar lesions which have appeared after this time are used as a scale for assessing the efficacy of the test substances.

b) Preventive-systemic Action

The active ingredient which is formulated as a wettable powder is introduced, at a concentration of 60 ppm (relative to the soil volume), onto the soil surface of three-week-old tomato plants cv. "Roter Gnom" in pots. After an interval of three days, the underside of the leaves is sprayed with a zoospore suspension of Phytophthora infestans. They are then kept for 5 days in a spray cabinet at 18 to 20° C. and saturated atmospheric humidity. After this time, typical foliar lesions appear whose number and size are used for assessing the efficacy of the test substances.

A good synergistic effect is shown, in particular, by active ingredient mixtures in which component I is

(35) methyl 2-[α-{[(α-methyl-3-trifluoromethylbenzyl)imino]oxy}-o-tolyl]glyoxylate O-methyloxime;

(32) methyl 2-[α-{[(α-methyl-3-trifluoromethoxybenzyl)imino]oxy}-o-tolyl]glyoxylate O-methyloxime;

(12) methyl 3-methoxy-2-[α-{[(α-methyl-3,4-methylenedioxybenzyl)imino]oxy}-o-tolyl]acrylate;

(15) methyl 2-[α-{[(α-cyclopropyl-4-chlorobenzyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(36) methyl 3-methoxy-2-[α-{[(α-cyclopropyl-4-chlorobenzyl)imino]oxy}-o-tolyl]acrylate; and component II is oxadixyl (II F), ofurace (II E), or in particular metalaxyl (II A) or R-metalaxyl (II B).

Example B-6: Residual-protective Action Against *Cercospora Arachidicola* in Goundnuts Groundnut plants 10 to 15 cm high are sprayed to drip point with an aqueous spray mixture (0.02% of active ingredient) and, 48 hours later, infected with a conidia suspension of the fungus. The plants are incubated for 72 hours at 21° and high atmospheric humidity and subsequently placed in a greenhouse until the typical foliar lesions appear. The activity of the active ingredient is assessed 12 days after the infection on the basis of number and size of the foliar lesions.

A markedly increased activity is shown, in particular, by active ingredient mixtures in which component I is

(32) methyl 2-[α-{[(α-methyl-3-trifluoromethoxybenzyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(15) methyl 2-[α-{[(α-cyclopropyl-4-chlorobenzyl)imino]oxy}-o-tolyl]glyoxylate O-methyloxime;

(18) methyl 3-methoxy-2-[α-{[(α-methyl-3-trifluoromethoxybenzyl)imino]oxy}-o-tolyl]acrylate; or

(36) methyl 3-methoxy-2-[α-{[(α-cyclopropyl-4-chlorobenzyl)imino]oxy}-o-tolyl]acrylate;

(38) methyl 2-[α-{[(α-cyclopropyl-4-trifluoromethoxybenzyl)imino]oxy}-o-tolyl]glyoxylate O-methyloxime or

(26) methyl 3-methoxy-2-[α-{[(α-methyl-4-chlorobenzyl)imino]oxy}-o-tolyl]acrylate.

Example B-7: Activity Against *Pyricularia Oryzae* in Rice a) Residual-protective Action Rice plants are grown for two weeks and then sprayed to drip point with an aqueous spray mixture (0.02% of active ingredient) and, 48 hours later, infected with a conidia suspension of the fungus. The fungus infestation is assessed 5 days after infection, during which a relative atmospheric humidity of 95 to 100% and a temperature of $22°$ are maintained.

b) Systemic Action

An aqueous spray mixture (0.006% of active ingredient based on the soil volume) is poured next to two-week-old rice plants. Care is taken that the spray mixture does not come into contact with aerial parts of the plants. The pots are then filled with water to such an extent that the bottom-most portions of the rice plant stalks are submerged After 96 hours, the plants are infected with conidia suspension of the fungus and kept for 5 days at a relative atmospheric humidity of 95 to 100% and a temperature of 24° C.

Active ingredient mixtures according to the invention show an increased activity against Pyricularia.

Example B-8: Activity Against *Botrytis Cinerea* on Apple Fruits. Residual-protective Action Artificially damaged apples are treated by applying a spray mixture (0.02% of active ingredient) dropwise to the site of damage. The treated fruits are subsequently inoculated with a spore suspension of the fungus and incubated for one week at high atmospheric humidity and approximately 20° C. The fungicidal activity of the test substance is deduced from the number of the sites of damage where rotting has been observed A markedly increased activity is shown in particular by active ingredient mixtures in which component I is

(09) methyl 2-[α-{[(α-cyclopropyl-4-fluorobenzyl)imino]oxy}-o-tolyl]glyoxylate O-methyloxime;

(32) methyl 2-[α-{[(α-methyl-3-trifluoromethoxybenzyl)imino]oxy}-o-tolyl]glyoxylate O-methyloxime;

(35) methyl 2-[α-{[(α-methyl-3-trifluoromethylbenzyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(15) methyl 2-[α-{[(α-cyclopropyl-4-chlorobenzyl)imino]oxy}-o-tolyl]glyoxylate O-methyloxime;

(18) methyl 3-methoxy-2-[α-{[(α-methyl-3-trifluoromethoxybenzyl)imino]oxy}-o-tolyl]acrylate; or

(36) methyl 3-methoxy-2-[α-{[(α-cyclopropyl-4-chlorobenzyl)imino]oxy}-o-tolyl]acrylate; and in which component II is furalaxyl (II C), metalaxyl (II A) or R-metalaxyl (II B).

Example B-9: Activity Against *Helminthosporium Gramineum*

Wheat kernels are contaminated with a spore suspension of the fungus and allowed to dry. The contaminated kernels are dressed with a suspension of the test substance (600 ppm of active ingredient based on the seed weight). After two days, the kernels are arranged in suitable agar dishes and, after a further four days, the development of fungal colonies around the kernels is assessed. Number and size of the fungal colonies are used for assessing the test substance. Active ingredient mixtures according to the invention show a markedly increased activity.

Example B-10: Activity Against *Fusarium Nivale* in Rye

Rye cv. Tetrahell which has been infected naturally with *Fusarium nivale* is dressed with the test fungicide in a roller mixer, the following concentrations being used: 20 or 6 ppm of a.i. (based on the seed weight). The infected and treated rye is sown in the open in October in plots of 3 m length and 6 seed rows, using a seed drill. 3 replications per concentration. Until the disease level is evaluated, the experimental field is subjected to the field conditions of normal crop management (preferably in a region with unbroken snow cover during the winter months). To assess the phytotoxicity, seedling emergence is scored in autumn and plant density/tillering in spring.

To assess the activity of the active ingredient, the percentage of Fusarium-infected plants is evaluated early in the year, immediately after the snows have melted.

A good synergistic effect is shown, in particular, by active ingredient mixtures in which component I is

(26) methyl 3-methoxy-2-[α-{[(α-methyl-4-chlorobenzyl)imino]oxy}-o-tolyl]acrylate;

(32) methyl 2-[α-{[(α-methyl-3-trifluoromethoxybenzyl)imino]oxy}-o-tolyl]glyoxylate O-methyloxime;

(18) methyl 3-methoxy-2-[α-{[(α-methyl-3-trifluoromethoxybenzyl)imino]oxy}-o-tolyl]acrylate;

(6) methyl 2-[α-{[(α-methyl-3,4-(difluoromethylenedioxy)benzyl)imino]oxy}-o-tolyl]glyoxylate O-methyloxime;

(38) methyl 2-[α-{[(α-cyclopropyl-4-trifluoromethoxybenzyl)imino]oxy}-o-tolyl]glyoxylate O-methyloxime.

Example B-11: Activity Against *Septoria Nodorum* in Wheat

Wheat plants in the 3-leaf stage are sprayed with a spray mixture (60 ppm of a.i.) prepared with a wettable powder of the active ingredient. After 24 hours, the treated plants are infected with a conidia suspension of the fungus. The plants are subsequently incubated for 2 days at a relative atmospheric humidity of 90–100% and placed for a further 10 days in a greenhouse at 20–24° C. 13 days after the infection, the fungus infestation is assessed. A markedly increased activity is shown, in particular, by active ingredient mixtures in which component I is

(32) methyl 2-[α-{[(α-methyl-3-trifluoromethoxybenzyl)imino]oxy}-o-tolyl]glyoxylate O-methyloxime;

(25) methyl 2-[α-{[(α-methyl-4-chlorobenzyl)imino]oxy}-o-tolyl]glyoxylate O-methyloxime;

(35) methyl 2-[α-{[(α-methyl-3-trifluoromethylbenzyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(36) methyl 3-methoxy-2-[α-{[(α-cyclopropyl-4-chlorobenzyl)imino]oxy}-o-tolyl]acrylate.

Example B-12: Activity Against Phytophthora in Potato Plants a) Residual-protective Action 2–3 week old potato plants (Bintje variety) are grown for 3 weeks and then sprayed with a spray mixture (0.02% of active ingredient) prepared with a wettable powder of the active ingredient. After 24 hours, the treated plants are infected with a sporangia suspension of the fungus. The fungus infestation is assessed after the infected plants have been incubated for 5 days at a relative atmospheric humidity of 90–100% and 20° C.

b) Systemic Action

A spray mixture (0.002% of active ingredient based on the soil volume) prepared with a wettable powder of the active ingredient is poured next to 2–3 week old potato plants (Bintje variety) which have been grown for 3 weeks. Care is taken that the spray mixture does not come into contact with the aerial parts of the plants. After 48 hours, the treated plants are infected with a sporangia suspension of the fungus. Fungus infestation is assessed after the infected plants have been incubated for 5 days at a relative atmospheric humidity of 90–100% and 20° C.

A good synergistic effect is shown, in particular, by active ingredient mixtures in which component I is

(32) methyl 2-[α-{[(α-methyl-3-trifluoromethoxybenzyl)imino]oxy}-o-tolyl]glyoxylate O-methyloxime;

(6) methyl 2-[α-{[(α-methyl-3,4-(difluoromethylenedioxy)benzyl)imino]oxy}-o-tolyl]glyoxylate O-methyloxime.

(15) methyl 2-[α-{[(α-cyclopropyl-4-chlorobenzyl)imino]oxy}-o-tolyl]glyoxylate O-methyloxime;

(24) methyl 3-methoxy-2-[α-{[(α-methyl-3-trifluoromethylbenzyl)imino]oxy}-o-tolyl]acrylate;

(12) methyl 3-methoxy-2-[α-{[(α-methyl-3,4-methylenedioxybenzyl)imino]oxy}-o-tolyl]acrylate;

(18) methyl 3-methoxy-2-[α-{[(α-methyl-3-trifluoromethoxybenzyl)imino]oxy}-o-tolyl]acrylate; or

(35) methyl 2-[α-{[(α-methyl-3-trifluoromethylbenzyl)imino]oxy}-o-tolyl]glyoxylate O-methyloxime;

in particular in a combination with metalaxyl (II A), benalaxyl (II D) or R-metalaxyl (II B).

Example B-13: Activity Against *Pythium Debardmanum* in Sugar Beet (*Beta vulgaris*)

a) Activity Following Soil Application

The fungus is grown on sterile oat kernels and added to a mixture of soil and sand. This infected soil is filled into flower pots and sugar beet seeds are sown. Immediately after sowing, the test preparations, formulated as wettable powders, are poured over the soil in the form of an aqueous suspension. The pots are then placed in the greenhouse for 2–3 weeks at 20–24° C. The soil is constantly kept uniformly moist by gently spraying with water. When evaluating the tests, the emergence of the sugar beet plants and the proportion of healthy and diseased plants are determined.

b) Activity Following Seed Dressing

The fungus is grown on sterile oat kernels and added to a mixture of soil and sand. This infected soil is filled into flower pots and sugar beet seeds which had been treated with the test preparations formulated as seed-dressing powders. The pots in which the seeds had been sown were placed in the greenhouse for 2–3 weeks at 20–24° C. The soil is kept uniformly moist by gently spraying with water. When evaluating tests, the emergence of the sugar beet plants and the proportion of healthy and diseased plants are determined.

The plants treated with the mixtures according to the invention are healthy in appearance, while the few untreated plants which emerge look unhealthy. Preferred active ingredient components I are

(12) methyl 3-methoxy-2-[α-{[(α-methyl-3,4-methylenedioxybenzyl)imino]oxy}-o-tolyl]acrylate;

(15) methyl 2-[α-{[(α-cyclopropyl-4-chlorobenzyl)imino]oxy}-o-tolyl]glyoxylate O-methyloxime;

(18) methyl 3-methoxy-2-[α-{[(α-methyl-3-trifluoromethoxybenzyl)imino]oxy}-o-tolyl]acrylate;

(24) methyl 3-methoxy-2-[α-{[(α-methyl-3-trifluoromethylbenzyl)imino]oxy}-o-tolyl]acrylate;

(29) methyl 3-methoxy-2-[α-{[(α-methyl-3,4-(difluoromethylenedioxy)benzyl)imino]oxy}-o-tolyl]acrylate;

(35) methyl 2-[α-{[(α-methyl-3-trifluoromethylbenzyl)imino]oxy}-o-tolyl]glyoxylate O-methyloxime and

(37) methyl 2-[α-{[(α-cyclopropyl-4-trifluoromethylbenzyl)imino]oxy}-o-tolyl]glyoxylate O-methyloxime.

Preferred active ingredient components II are benalaxyl (II D), ofurace (II E), oxadixyl (II F), but preferably metalaxyl (II A) and R-metalaxyl (II B).

What is claimed is:

1. A composition comprising synergistic microbiocidally effective amounts of at least two active ingredient components together with a suitable carrier material, wherein component I is a compound of the formula I

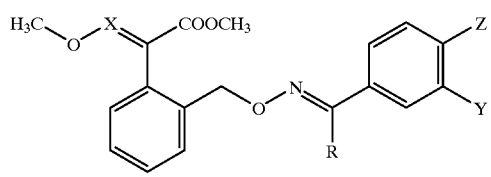

in which:

X is N;

R is $CH_3$;

Y is $CF_3$;

Z is H;

and wherein component II is a compound selected from the group consisting of

II A) metalaxyl,

II B) R-metalaxyl,

II C) furalaxyl,

II D) benalaxyl,

II E) ofurace, and

II F) oxadixyl;

and wherein the ratio by weight I:II is 25:1 to 1:20.

2. The composition according to claim 1, wherein component II is metalaxyl or R-metalaxyl.

3. The composition according to claim 1, wherein the weight ratio of I:II is from 20:1 to 1:10.

4. The composition according to claim 3, wherein the weight ratio of I:II is from 12:1 to 1:8.

5. A method of controlling or preventing plant diseases, which comprises treating a plant, plant part, plant propagation material, seed or their locus infested with, or at risk from, disease causing fungi with a synergistic fungicidally effective combined amount of the composition comprising component I and component II according to claim 1, in any sequence or simultaneously.

6. The method according to claim 5, wherein plants, plant propagation material, seeds or parts of plants are at risk from Oomycetes.

7. A method according to claim 5, wherein grapevines are treated.

8. A method according to claim 5, wherein potatoes are treated.

9. A method according to claim 5, wherein vegetables and fruit are treated.

10. A method according to claim 5, wherein plant propagation material is treated.

* * * * *